United States Patent

Bryant et al.

Patent Number: 5,821,253
Date of Patent: Oct. 13, 1998

[54] TETRAHYDROBENZO[A]FLUORENE COMPOUNDS AND METHODS OF USE

[75] Inventors: Henry Uhlman Bryant, Indianapolis; George Joseph Cullinan, Trafalgar, both of Ind.

[73] Assignee: Eli Lilly and Company, Indianapolis, Ind.

[21] Appl. No.: 937,646

[22] Filed: Sep. 24, 1997

[51] Int. Cl.$^6$ .............. C07D 211/08; A61K 31/445
[52] U.S. Cl. ............. 514/319; 514/212; 514/428; 514/650; 514/239.2; 540/609; 546/195; 548/528; 564/337; 544/154
[58] Field of Search ............. 564/337; 540/609; 546/195; 548/528; 514/212, 319, 428, 650

[56] References Cited

U.S. PATENT DOCUMENTS

| | | | |
|---|---|---|---|
| 3,274,213 | 9/1966 | Lednicer et al. | 260/326.5 |
| 3,394,125 | 7/1968 | Crenshaw | 260/326.5 |
| 3,413,305 | 11/1968 | Crenshaw | 260/326.5 |
| 4,133,814 | 1/1979 | Jones et al. | 260/326 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,147,880 | 9/1992 | Jones et al. | 514/650 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |
| 5,484,795 | 1/1996 | Bryant et al. | 514/212 |

FOREIGN PATENT DOCUMENTS

| | | |
|---|---|---|
| 062 503 | 10/1982 | European Pat. Off. . |
| WO 89/0289 | 4/1989 | WIPO . |
| WO 95/10513 | 4/1995 | WIPO . |

OTHER PUBLICATIONS

Crenshaw, R.R., et al, *J. Med. Chem.* 14(12):1185–1190 (1971).
Jones, C.D., et al, *J. Med. Chem.* 27: 1057–1066) 1984.
Jones, C.D., et al, *J. Med. Chem.* 35: 931–938 1992.

*Primary Examiner*—Bernard Dentz
*Attorney, Agent, or Firm*—Janelle D. Strode; David E. Boone

[57] ABSTRACT

The invention provides tetrahydrobenzo[a]fluorene compounds, formulations, and methods of inhibiting bone loss or bone resorption, particularly osteoporosis, and cardiovascular-related pathological conditions, including hyperlipidemia.

11 Claims, No Drawings

TETRAHYDROBENZO[A]FLUORENE COMPOUNDS AND METHODS OF USE

BACKGROUND OF THE INVENTION

This application claims the benefit of U.S. Provisional application Ser. No. 60/026,752 filed Sep. 26, 1996.

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

The instant invention provides tetrahydrobenzo[a]fluorene compounds, pharmaceutical formulations thereof, and methods of using such compounds for the treatment of postmenopausal syndrome and other estrogen-related pathological conditions such as those mentioned below.

SUMMARY OF THE INVENTION

The instant invention relates to compounds of formula I:

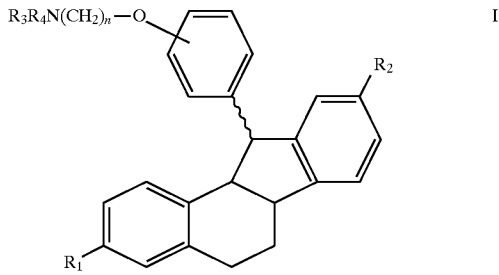

wherein:

$R_1$ is —H, —OH, —O($C_1$-$C_4$ alkyl), —OCO($C_1$-$C_6$ alkyl), —O(CO)O($C_1$-$C_6$ alkyl), —COAr, —OCOAr, —O(CO)OAr, where Ar is phenyl or optionally substituted phenyl, or —OSO$_2$—($C_4$-$C_6$ alkyl);

$R_2$ is —OH, —O($C_1$-$C_4$ alkyl), —OCO($C_1$-$C_6$ alkyl), —O(CO)O($C_1$-$C_6$ alkyl), —COAr, —OCOAr, —O(CO)OAr, where Ar is phenyl or optionally substituted phenyl, or —OSO$_2$—($C_4$-$C_6$ alkyl);

$R_3$ and $R_4$ are each independently —$C_1$-$C_4$ alkyl, or combine to form 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino;

n is 2 or 3;

or a pharmaceutically acceptable salt or solvate thereof.

The instant invention further provides pharmaceutical formulations containing compounds of formula I, and the use of said compounds at least for the inhibition of bone loss or bone resorption, particularly osteoporosis and cardiovascular-related pathological conditions, including hyperlipidemia, and other cardiovascular pathologies.

DETAILED DESCRIPTION OF THE INVENTION

General terms used in the description of compounds herein described bear their usual meanings. For example, "$C_1$-$C_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—$OC_1$–$C_4$ alkyl" represents a $C_1$–$C_4$ alkyl group attached through an oxygen such as, for example, methoxy, ethoxy, n-propoxy, isopropoxy, and the like. Of these $C_1$–$C_4$ alkoxy groups, methoxy is preferred.

The term "substituted phenyl" refers to a phenyl group having one or more substituents selected from the group consisting of $C_1$–$C_4$ alkyl, —$OC_1$–$C_4$ alkyl, hydroxy, nitro, chloro, fluoro, or tri(chloro or fluoro)methyl.

The term "hydroxy protecting group" contemplates numerous functionalities used in the literature to protect a hydroxyl function during a chemical sequence and which can be removed to yield the phenol. Included within this group would be acyls, mesylates, tosylates, benzyl, alkylsilyloxys, —$OC_1$–$C_4$ alkyls, and the like. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965).

The term "substituted phenyl" refers to a phenyl group having one or more substituents selected from the group consisting of $C_1$–$C_4$ alkyl, $C_1$–$C_3$ alkoxy, hydroxy, nitro, chloro, fluoro, or tri(chloro or fluoro)methyl. "$C_1$–$C_3$ alkoxy" refers a $C_1$–$C_3$ alkyl group attached through an oxygen bridge such as, methoxy, ethoxy, n-propoxy, isopropoxy.

The term "solvate" represents an aggregate that comprises one or more molecules of the solute, such as a formula I compound, with one or more molecules of solvent.

The term "inhibit" includes its generally accepted meaning which includes prohibiting, preventing, restraining, and slowing, stopping, or reversing progression, severity, or ameliorating a resultant symptom or effect.

Compounds of the present invention are named as derivatives of benzo[a]fluorene in accordance to the Ring Index, The American Chemical Society, as follows:

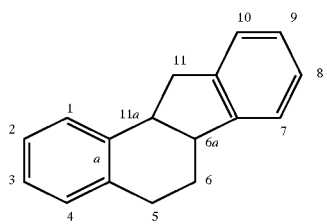

Thus, a compound of formula I, wherein $R_1$ and $R_2$ are methoxy, $R_3$ and $R_4$ combine to form 1-piperidinyl, and n is two, is named as follows:
1-[2-[4-(6,6a,11,11a-tetrahydro-3,9-dimethoxy-5H-benzo[a]fluoren-11-yl)phenoxy]ethyl]piperidine. Additional representative compounds of the instant invention include 1-[2-[4-(6,6A,11,11A-tetrahydro-9-methoxy-5H-benzo[a]fluoren-11-yl)phenoxy]ethyl]pyrrolidine, 1-[2-[4-(6,6A,11,11A-tetrahydro-9-methoxy-5H-benzo[a]fluoren-11-yl)phenoxy]ethyl]piperidine, and 1-[2-[4-(6,6A,11,11A-tetrahydro-3,9-dimethoxy-5H-benzo[a]fluoren-11-yl)phenoxy]ethyl]pyrrolidine.

Included within the scope of the invention are the various stereochemical isomers at the 6A, 11, and 11A carbon atoms.

Compounds of formula I may be prepared from their corresponding 3,4-dihydronaphthylmethanol precursors, such as, for example, a compound of formula II, by a chemically unique rearrangement and reduction.

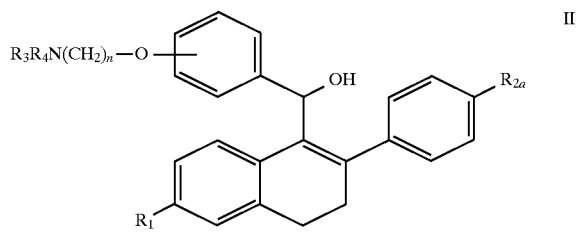

wherein:

$R_{2a}$ is hydroxy or —$O(C_1$–$C_4$ alkyl); and $R_1$, $R_3$, $R_4$, and n have their previous meanings.

A compound of formula II is treated with a trialkylsilane reducing agent, such as triethylsilane, in the presence of a strong acid, such as trifloroacetic acid, in THF at ambient temperature. The strong acid protonates the secondary alcohol, which then undergoes the elimination of water, thus generating a carbonium ion. The 1,2 double bond of the dihydronaphthyl system migrates to the exocyclic position, regenerating the carbonium ion at the 2-position of the naphthyl system. The system then undergoes a rearrangement, whereby the exo-cyclic double bond migrates to form a bridge between the carbinol carbon and the 2-position of the phenyl ring, thus forming the benzo[a]fluorenyl system. At the same time, the hydrogen on the 2-position of the phenyl ring undergoes a 1,3 shift to the 2-position of the naphthalene. This re-arrangement generates the benzo[a]fluorenyl system with the carbonium ion at the 11a-position. The final ion is then reduced by the silane to yield the final product, as illustrated in Scheme I below. As a result of the mechanism of this reaction, the stereochemical centers are not stereochemically controlled, thus resulting in a mixture of isomers (for example, the 6a, 11, and 11a-positions). $R_{2a}$ in formula II must be hydroxy or —$O(C_1$–$C_4$ alkyl), with methoxy being preferred. If other substituents are used, the above-described reaction does not occur, but instead, the compounds of formula II form naphthalenes via the elimination of water and aromatization.

Scheme I

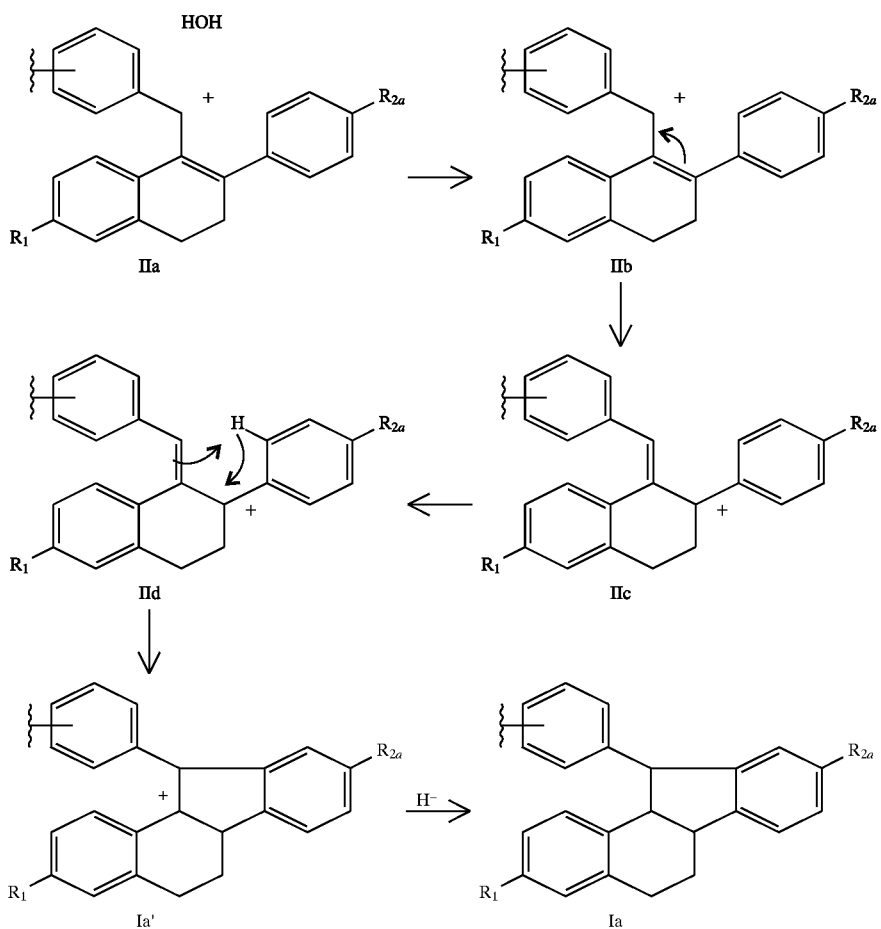

The compounds of formula II are obtained by a reduction of a compound of formula III with LiAlH$_4$, NaBH$_4$, or the like, in an appropriate solvent at temperatures of 0°–30° C. The methods for this reduction are disclosed in U.S. Pat. No. 5,484,797, the disclosure of which is herein incorporated by reference.

The compounds of formula III are synthesized by methods known in the art.

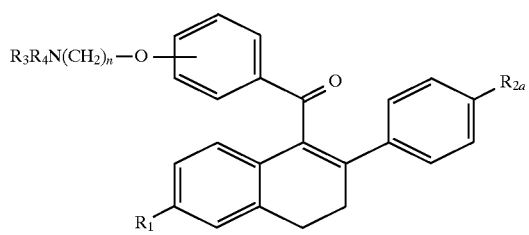

wherein $R_1$, $R_{2a}$, $R_3$, $R_4$, and n have their previous meanings.

Specifically, the compounds of formula III, wherein $R_{2a}$ is —O($C_1$–$C_4$ alkyl) or —OH and the basic side chain is in the 4(para)-position of the benzoyl moiety, are synthesized by methods as provided in U.S. Pat. Nos. 4,230,862 and 5,147,880 and also in Jones, C. D., et al., *J. Med. Chem.*, 22, 962–966 (1979) and Jones C. D., et al.,*J. Med. Chem.* 35(5), 931–938 (1992), the disclosures of each of which are herein incorporated by reference. The compounds of formula III, wherein $R_{2a}$ is —O($C_1$–$C_4$ alkyl) or —OH and the basic side chain is in the 3(meta)-position of the benzoyl moiety, are synthesized from a compound of formula IV via the methods of Jones, ibid.

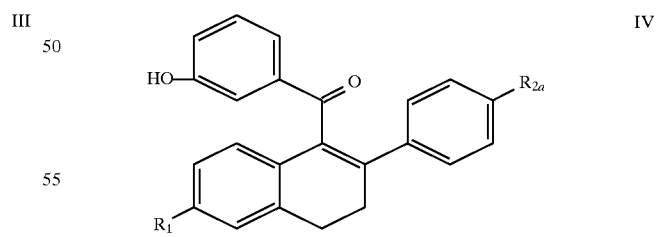

wherein $R_1$ and $R_{2a}$ have their previous meanings.

The compounds of formula IV may be prepared by the methods of Jones, ibid. starting with the reaction of the appropriate beta-tetralone with sodium hydride and 3-benzyloxybenzoyl phenylester to form a compound of formula V.

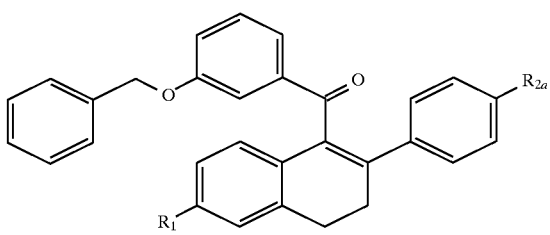

wherein $R_1$ and $R_{2a}$ have their previous meanings.

A compound of formula V is then converted to a compound of formula IV by removal of the benzyl protecting group with catalytic hydrogenation, typically by refluxing in 10% EtOH in toluene with tetrakis(triphenylphosphine) palladium (0) for several hours (See: Barton, J. W., "Protective Groups in Organic Chemistry", McOhmie, W. Ed., Plenum Press, NYC, 1973, Chapter 2 or Green, T. W., "Protective Groups in Organic Synthesis", John Wiley and Sons, NYC, 1981, Chapter 7.) Other derivatives of formula I wherein $R_1$ and $R_2$ are esters of sulfonates are prepared from the phenolic starting material by methods known in the art, such as, for example U.S. Pat. No. 5,393,763, the disclosure of which is herein incorporated by reference. The phenols are prepared from the methoxy precursors by de-alkylation with $AlCl_3$ and EtSH in $CH_2Cl_2$ via methods as described in Jones supra.

Although the free-base form of formula I compounds can be used in the methods of the instant invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting, alleviating, ameliorating, treating, or preventing further symptoms in mammals, including humans, suffering from bone loss or bone resorption, particularly osteoporosis, and cardiovascular-related pathological conditions including hyperlipidemia and related cardiovascular pathologies.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissollution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to treat, inhibit, or prevent the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg, from one to three times per day. Such dosages will be administered to a patient in need thereof usually at least for thirty days, and more typically for six months, or chronically.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1

Gelatin Capsules

| Ingredient | Quantity (mg/capsule) |
| --- | --- |
| Active Ingredient | 0.1-1000 |
| Starch NF | 0-500 |
| Starch flowable powder | 0-500 |
| Silicone fluid 350 centistokes | 0-15 |

The ingredients are blended, passed through a No. 45 mesh U.S. sieve, and filled into hard gelatin capsules.

Formulation 2

Tablets

| Ingredient | Quantity (mg/tablet) |
| --- | --- |
| Active Ingredient | 2.5-1000 |
| Starch | 10-50 |
| Cellulose, microcrystaliine | 10-20 |
| Polyvinylpyrrolidone (as 10% solution in water) | 5 |
| Sodium carboxymethylcellulose | 5 |
| Magnesium stearate | 1 |
| Talc | 1-5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50°–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3

Aerosol

| Ingredient | Weight % |
| --- | --- |
| Active Ingredient | 0.25 |
| Ethanol | 29.75 |
| Propellant 22 (Chloradifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Suppositories

| Ingredient | Weight |
| --- | --- |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5

Suspension

Suspensions each containing 0.1–1000 mg of a compound of formula I per 5 mL dose.

| Ingredient | Weight |
| --- | --- |
| Active Ingredient | 0.1–1000 mg |
| Sodium carboxymethyl cellulose | 50 mg |
| Syrup | 1.25 mL |
| Benzoic acid solution (0.1M) | 0.10 mL |
| Flavor | q.v |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following Examples and Preparations are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

EXAMPLES

Preparation 1

[2-(4-Methoxyphenyl)-3,4-dihydronaphth-1-yl][4-(1-pyrrolidinyl-2-ethoxy)phenyl]carbinol 850 mg (1.9 mmol) of [2-(4-methoxyphenyl)-3,4-dihydronaphth-1-yl][4-(1-pyrrolidinyl-2-ethoxy)phenyl]methanone was dissolved in 100 mL of THF and 160 mg (4 mmol) of $LiAlH_4$ was added. The reaction mixture was stirred at room temperature and under a $N_2$ atmosphere for eighteen hours. The reaction mixture was evaporated to dryness in vacuo. Fifty mL of water was carefully added to the residue and the reaction mixture was extracted twice with 100 mL of EtOAc. The EtOAc extracts were combind and washed with water, then the EtOAc layer was removed and dried by filteration through anhydrous $Na_2SO_4$ and evaporated to dryness in vacuo. This yielded 670 mg of the title compound as a white amorphous powder.
PMR: consistent with the proposed structure
MS: m/e=455 (M+) FD
EA: Calc: C,79.2; H,7.26; N,3.08 Found: C,79.11; H,7.47; N, 2.93
$C_{30}H_{33}NO_3$
$R_f$=0.46 silica gel eluted with $CHCl_3$-MeOH (19:1)

Example 1

1-[2-[4-(6,6A,11,11A-Tetrahydro-9-methoxy-5H-benzo[a]fluoren-11-yl)phenoxy]ethyl]pyrrolidine 1.8 g (0.004 mol) of [2-(4-methoxyphenyl)-3,4-dihydronaphth-1-yl][4-(1-pyrrolidinyl-2-ethoxy)phenyl]carbinol was dissolved in 100 mL of $CH_2Cl_2$ and 0.6 g (0.005 mol) of $Et_3SiH$ was added. The reaction mixture was stirred for several minutes under a $N_2$ atmosphere. 25 mL of $CF_3COOH$ was slowly added and the reaction was allowed proceed for eighteen hours at room temperature. The reaction mixture was evaporated to dryness in vacuo. The reaction residue was dissolved in 100 mL of hot water and 25 mL of MeOH. This solution was made basic with the addition of saturated aqueous $NaHCO_3$ solution and extracted twice with 100 ml portions of EtOAc. The EtOAc extracts were combind and dried by filteration through anhydrous $Na_2SO_4$ and evaporated to dryness in vacuo. This resulted in 1.23 g of the title compound as a tan, amorphous powder.
$R_f$=0.62 silica gel eluted with $CHCl_3$-MeOH (19:1)

Example 2

1-[2-[4-(6,6A,11,11A-Tetrahydro-9-methoxy-5H-benzo[a]fluoren-11-yl)phenoxy]ethyl]pyrrolidine hydrochloride 1.23 g of 1-[2-[4-(6,6A,11,11A-tetrahydro-9-methoxy-5H-benzo[a]fluoren-11-yl)phenoxy]ethyl]pyrrolidine was dissolved in 10 mL of EtOAc and a saturated solution of HCl-$Et_2O$ was added until the product stopped precipitating out. The liquid was decanted off and the remaining solid was triturated (2×) with $Et_2O$. The solid was dried in vacuo at room temperature for several hours. This resulted in 960 mg of the title comkpound as a pink, amorphous powder.
PMR: consistent with the proposed structure
EA: Calc: C,75.69; H,7.20; N,2.94 Found: C,75.42; H,7.43; N,2.85
$C_{30}H_{34}ClNO_2$ Example 3

[2-(4-Methoxyphenyl)-3,4-dihydro-6-methoxylnaphth-1-yl][4-(1-piperidinyl-2-ethoxy)phenyl]carbinol 4.45 g (0.009 mol) of [2-(4-methoxyphenyl)-3,4-dihydro-6-methoxynaphth-1-yl][4-(1-piperidinyl-2-ethoxy) phenyl]methanone was dissolved in 100 mL of THF and 1 g (0.026 mol) of $LiAlH_4$ was carefully added. The reaction mixture was stirred at room temperature and under $N_2$ for eighteen hours. The reaction mixture was evaporated to dryness and 100 mL of water was carefully added. The reaction mixture was extracted twice with 100 mL portions of EtOAc. The combind EtOAc extracts were dried by filteration through anhydrous $Na_2SO_4$. The EtOAc extract was evaporated to dryness in vacuo. This yielded 3.38 g of the title compound as a white, amorphous powder.
MS: m/e=500 (M+1) FD
$R_f$=0.55 silica gel eluted with $CHCl_3$-MeOH (19:1)

Example 4

1-[2-[4-(6,6A,11,11A-Tetrahydro-3,9-dimethoxy-5H-benzo[a]fluoren-11-yl)phenoxy]ethyl]piperidine 2.5 g (0.005 mol) of [2-(4-Methoxyphenyl)-3,4-dihydro-6-methoxylnaphth-1-yl][4-(1-piperidinyl-2-ethoxy)phenyl]carbinol was dissolved in 100 mL of $CH_2Cl_2$ and 810 mg (0.007 mol) of $Et_3SiH$ was added. The reaction mixture was stirred at room temperature and under $N_2$ for several minutes. 12 mL of $CF_3COOH$ was slowly added. The reaction was allowed to proceed for thirty-six hours. The reaction mixture was evaporated to dryness. The reaction mixture was dissolved in 100 mL of $CH_2Cl_2$ and was washed with 100 mL of 1N NaOH and the $CH_2Cl_2$ layer was removed. The $CH_2Cl_2$ solution was dried by filteration through anhydrous $Na_2SO_4$ and evaporated to dryness. The residue was crystallized from EtOAc and Hexane. This resulted in 240 mg of the title compound as a white crystalline powder.
PMR: consistent with the proposed structure
MS: m/e=484 (M+) FD
EA: Calc: C, 79.47; H,7.71; N,2.90 Found: C,75.14; H,7.28; N,2.94
$C_{32}H_{37}NO_3$ Example 5

[2-(4-Methoxyphenyl)-3,4-dihydronaphth-1-yl][4-(1-piperidinyl-2-ethoxy)phenyl]carbinol 2 g (0.00335 mol) of [2-(4-methoxyphenyl)-3,4-dihydronaphth-1-yl](4-(1-piperidinyl-2-ethoxy)phenyl]methanone mesylate was suspended in 100 mL of THF. 1 g (0.026 mol) of $LiAlH_4$ was slowly added and the reaction was stirred and allowed to proceed at room temperature and under $N_2$ for eighteen hours. The reaction mixture was evaporated to dryness in vacuo. 100 mL of EtOAc was added and 50 mL of water was slowly added. The EtOAc layer was removed and the cloudy aqueous layer was extracted twice more with 100 mL portions of EtOAc. All of the EtOAc extracts were combined and dried by filteration through anhydrous $Na_2SO_4$ and evaporated to dryness. The resulting, glassy residue was chromatographed (HPLC) on a silica gel column eluted with a linear gradient starting with $CHCl_3$ and ending with $CHCl_3$-MeOH (3:1, v/v). The fractions containing the desired product were determined by tlc and combind and evaporated to dryness. This resulted in 1 g of the title compound as a white, amorphous powder.
PMR: consistent with the proposed structure
MS: m/e=469 (M+) FD
$R_f$=0.62 silica gel eluted with $CHCl_3$-MeOH (19:1)

Example 6

1-[2-[4-(6, 6A,11,11A-Tetrahydro-9-methoxy-5H-benzo[a]fluoren-11-yl)phenoxy]ethyl]piperidine 1 g (0.002 mol) of [2-(4-methoxyphenyl)-3,4-dihydronaphth-1-yl][4-(1-piperidinyl-2-ethoxy)phenyl]carbinol was dissolved in 50 mL of $CH_2Cl_2$ and 460 mg (0.004 mol) of $Et_3SiH$ was added. The reaction mixture was stirred for several minutes at room temperature and under $N_2$. 12 mL of $CF_3COOH$ was slowly added. The reaction was allowed to proceed for seventy-two hours. The reaction mixture was evaporated to dryness. 50 mL of $CH_2Cl_2$ was added and the solution was extracted with 50 mL of 1N NaOH. The organic layer was dried with $Na_2SO_4$ and evaporated to dryness. The residue was crystallized from $Et_2O$-Hexane. This resulted in 270 mg of the title compound as a tan, crystaline powder.
PMR: consistent with the proposed structure
MS: 454 (M+) FD
EA: Calc: C, 82.08; H, 7.78; N, 3.09 Found: C, 81.95; H, 7.87; N, 3.10
$C_{31}H_{35}NO_2$ Test Procedures In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at $22.2°\pm1.7°$ C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17α-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: Xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotemetrically at 500 nm. Cholesterol concentration was then calculated against a standard curve.

Uterine Eosinophil Peroxidase (EPO) Assay. Uteri were kept at 4° C. until time of enzymatic analysis. The uteri were then homogenized in 50 volumes of 50 mM Tris buffer (pH - 8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound: 17α-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17α-ethynyl estradiol ($EE_2$; an orally available form of estrogen), and rats treated with certain compounds of the instant invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Table 1 below reflects the response of 5 to 6 rats per treatment.

TABLE 1

| Compound No. | Dose mg/kg[a] | Uterine Weight % Inc[b] | Uterine Eosinophil (Vmax)[c] | Serum Cholest. % Dec.[d] |
|---|---|---|---|---|
| $EE_2$[e] | 0.1 | 206.1* | 155.2* | 97.9* |
| Compound 3 | 0.1 | 47.9* | 28.1* | 58.6* |
|  | 1.0 | 53.3* | 92.8* | 65.9* |
|  | 10.0 | 97.6* | 64.0* | 52.4* |
| Compound 5 | 0.1 | 59.4* | 15.7 | 41.8* |
|  | 1.0 | 43.3* | 55.4* | 55.2* |
|  | 10.0 | 109.2* | 50.9* | 51.8* |
| Compound 7 | 0.1 | 18 | 4.3 | 40.5* |
|  | 1.0 | 67.5* | 46.3* | 69.6* |
|  | 10.0 | 77.7* | 43.2* | 47.4* |

[a] mg/kg PO
[b] Uterine Weight % increase versus the ovariectomized controls
[c] Eosinophil peroxidase Vmax
[d] Serum aholesterol decrease versus ovariectomized controls
[e] 17-α-Ethynyl estradiol
*p < .05

In addition to the demonstrated benefits of the compounds of the instant invention, the above data clearly demonstrate that compounds of Formula I are not estrogen mimetics. Furthermore, no deleterious toxicological effects (for example, survival numbers) were observed with any treatment.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the instant invention and ethynyl estradiol ($EE_2$) in 20% hydroxypropyl β-cyclodextrin are orally administered to test animals. Distal femur metaphysis and proximal tibiae data are the results of formula I compound treatments compared to intact and ovariectomized test animals. Results are reported as percent protection relative to ovariectomy.

We claim:

1. A compound of formula I:

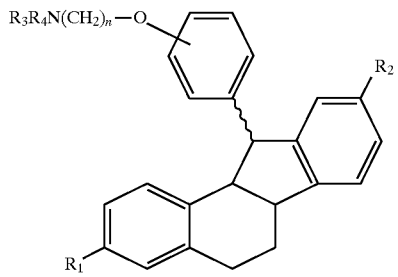

wherein:

$R_1$ is —H, —OH, —O($C_1$-$C_4$ alkyl), —OCO($C_1$-$C_6$ alkyl), —O(CO)O($C_1$-$C_6$ alkyl), —COAr, —OCOAr, —O(CO)OAr, where Ar is phenyl or optionally substituted phenyl, or —OSO$_2$—($C_4$-$C_6$ aklyl);

$R_2$ is —OH, —O($C_1$-$C_4$ alkyl), —OCO($C_1$-$C_6$ alkyl), —O(CO)O($C_1$-$C_6$ alkyl), —COAr, —OCOAr, —O(CO)OAr, where Ar is phenyl or optionally substituted phenyl, or —OSO$_2$—($C_4$-$C_6$ alkyl);

$R_3$ and $R_4$ are each independently —$C_1$-$C_4$ alkyl, or combine to form 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino;

n is 2 or 3;

or a pharmaceutically acceptable salt or solvate thereof.

2. A compound according to claim 1 wherein $R_1$ is —H and $R_2$ is —OH.

3. A compound according to claim 1 wherein $R_1$ is —H and $R_2$ is —OCH$_3$.

4. A compound according to claim 1 wherein $R_3$ and $R_4$ combine to form 1-piperidinyl.

5. A compound according to claim 1 wherein $R_3$ and $R_4$ combine to form 1-pyrrolidinyl.

6. A compound according to claim 1 which is the hydrochloride salt.

7. A compound according to claim 1 selected from the group consisting of

1-[2-[4-(6,6A,11,11A-tetrahydro-9-methoxy-5H-benzo[a]fluoren-11-yl)phenoxy]ethyl]pyrrolidine, 1-[2-[4-(6,6A,11,11A-tetrahydro-9-methoxy-5H-benzo[a]fluoren-11-yl)phenoxy]ethyl]piperidine, 1-[2-[4-(6,6A,11,11A-tetrahydro-3,9-dimethoxy-5H-benzo[a]fluoren-11-yl)phenoxy]ethyl]pyrrolidine, and 1-[2-[4-(6,6A,11,11A-tetrahydro-3,9-dimethoxy-5H-benzo[a]fluoren-11-yl)phenoxy]ethyl]piperidine.

8. A pharmaceutical formulation comprising a compound according to claim 1 in combination with a pharmaceutically acceptable carrier, diluent, or excipient.

9. A method of inhibiting bone loss or bone resorption which comprises administering to a patient in need thereof an effective amount of a compound of claim 1.

10. A method according to claim 9, wherein said bone loss or bone resorption is due to menopause or ovariectomy.

11. A method of lowering serum cholesterol levels which comprises administering to a patient in need thereof an effective amount of a compound of claim 1.

* * * * *